United States Patent
Shin et al.

(10) Patent No.: US 9,683,216 B2
(45) Date of Patent: Jun. 20, 2017

(54) METHOD FOR PREPARATION OF ARTIFICIAL BLOOD VESSEL USING TUBE-TYPE POROUS BIODEGRADABLE SCAFFOLD HAVING A DOUBLE-LAYERED STRUCTURE AND STEM CELL, AND ARTIFICIAL BLOOD VESSEL MADE BY THE SAME

(75) Inventors: Jung-Woog Shin, Busan (KR); Dong-Hwa Kim, Gimhae-si (KR)

(73) Assignee: INJE UNIVERSITY INDUSTRY-ACADEMIC COOPERATION FOUNDATION, Gimhae-si, Gyeongsangnam-Do (KR)

( * ) Notice: Subject to any disclaimer, the term of this patent is extended or adjusted under 35 U.S.C. 154(b) by 0 days.

(21) Appl. No.: 13/299,748

(22) Filed: Nov. 18, 2011

(65) Prior Publication Data

US 2012/0253456 A1 Oct. 4, 2012

Related U.S. Application Data

(63) Continuation of application No. PCT/KR2011/008816, filed on Nov. 17, 2011.

(30) Foreign Application Priority Data

Mar. 31, 2011 (KR) .................. 10-2011-0029816

(51) Int. Cl.
*C12N 5/071* (2010.01)
*A61F 2/06* (2013.01)

(52) U.S. Cl.
CPC ............ *C12N 5/0691* (2013.01); *A61F 2/062* (2013.01); *C12N 2501/105* (2013.01);
(Continued)

(58) Field of Classification Search
CPC ............ C12N 5/0691; C12N 2501/105; C12N 2501/11; C12N 2501/115;
(Continued)

(56) References Cited

U.S. PATENT DOCUMENTS

2006/0240061 A1* 10/2006 Atala et al. .................. 424/422

OTHER PUBLICATIONS

Hsu SH et al. (2005). The effect of dynamic culture conditions on endothelial cell seeding and retation on small diameter polyurethane vascular grafts. Medical Engineering and Physics, v27, p. 267-272.*

(Continued)

*Primary Examiner* — Scott Long
*Assistant Examiner* — Sean C Barron
(74) *Attorney, Agent, or Firm* — Lucas & Mercanti, LLP

(57) ABSTRACT

The present invention relates to a method for preparation of an artificial blood vessel using a tube-type porous biodegradable scaffold having a double layered structure and a stem cell, and an artificial blood vessel made by the same. Specifically, the present invention relates to a method for preparation of an artificial blood vessel by separately seeding a stem cell onto the inner membrane and an outer membrane of a tube-type porous biodegradable scaffold having a double layered structure, wherein the inner membrane and the outer membrane having different biodegradable polymer nano-fiber arrangements are continuously linked, and by inducing differentiation; and an artificial blood vessel made by the same.

6 Claims, 15 Drawing Sheets

(52) U.S. Cl.
CPC .... *C12N 2501/11* (2013.01); *C12N 2501/115* (2013.01); *C12N 2501/165* (2013.01); *C12N 2501/33* (2013.01); *C12N 2501/39* (2013.01); *C12N 2501/91* (2013.01); *C12N 2506/1353* (2013.01); *C12N 2521/00* (2013.01); *C12N 2527/00* (2013.01); *C12N 2533/30* (2013.01); *C12N 2533/40* (2013.01)

(58) Field of Classification Search
CPC .......... C12N 2501/165; C12N 2501/33; C12N 2501/91; C12N 2506/1353; C12N 2521/00; C12N 2527/00; C12N 2533/30; C12N 2533/40; C12N 2501/39; A61F 2/062
USPC .................................. 424/422, 9.34; 435/366
See application file for complete search history.

(56) References Cited

OTHER PUBLICATIONS

Nasseri BA et al. (2003). Dynamic Rotational Seeding and Cell Culture System for Vascular Tube Formation. Tissue Engineering, v9(2), p. 291-299.*

Inoguchi H et al. (2007). The effect of gradually graded shear stress on the morphological integrity of a huvec-seeded compliant small-diameter vascular graft. Biomaterials, v28, p. 486-495.*

Venugopal J et al. (2007). Interaction of Cells and Nanofiber scaffolds in Tissue Engineering. Journal of Biomedical Materials Research Part B: Applied Biomaterials, v84B(1), p. 34-48.*

Dong et al. (2009). Response of mesenchymal stem cells to shear stress in tissue-engineered vascular grafts. Acta Pharmacol Sin., v30(5), p. 530-536.*

Wang et al. (2005). Shear Stress Induces Endothelial Differentiation From a Murine Embryonic Mesenchymal Progenitor Cell Line. Arterioscler Thromb Vasc Biol., v25, p. 1817-1823.*

Kobayashi et al. (2004). Mechanical stress promotes the expression of smooth muscle-like properties in marrow stromal cells. Experimental Hematology, v32, p. 1238-1245.*

Park et al. (2004). Differential Effects of Equiaxial and Uniaxial Strain on Mesenchymal Stem Cells. Biotechnology and Bioengineering, v88(3), p. 359-368.*

Gimble et al. (2007). Adipose-Derived Stem Cells for Regenerative Medicine. Circulation Research, v100, p. 1249-1260.*

Vaz et al. (2005). Design of scaffolds for blood vessel tissue engineering using a multi-layering electrospinning technique. Acta Biomaterials, v1, p. 575-582.*

Hong et al. Next Generation of Electrosprayed Fibers for Tissue Regeneration. Tissue Eng Part B Rev. (epub. Feb. 16, 2011), v17(2), p. 125-142.*

* cited by examiner

METHOD FOR PREPARATION OF ARTIFICIAL BLOOD VESSEL USING TUBE-TYPE POROUS BIODEGRADABLE SCAFFOLD HAVING A DOUBLE-LAYERED STRUCTURE AND STEM CELL, AND ARTIFICIAL BLOOD VESSEL MADE BY THE SAME

CROSS-REFERENCE TO RELATED APPLICATIONS

This application is a continuation of PCT/KR2011/008816, filed Nov. 17, 2011, which claims the benefit of Korean Patent Application No. 10-2011-0029816, filed Mar. 31, 2011, the contents of each of which are incorporated herein by reference.

FIELD OF THE INVENTION

The present invention relates to a method for preparation of an artificial blood vessel using a tube-type porous biodegradable scaffold having a double layered structure and a stem cell, and an artificial blood vessel made by the same. Specifically, the present invention relates to a method for preparation of an artificial blood vessel by separately seeding a stem cell onto the inner membrane and an outer membrane of a tube-type porous biodegradable scaffold having a double layered structure using the tube-type porous biodegradable scaffold having a double layered structure, wherein the inner membrane and the outer membrane having different biodegradable polymer nano-fiber arrangements are continuously linked, and by inducing differentiation; and an artificial blood vessel made by the same.

BACKGROUND OF THE INVENTION

Blood vessel replacing materials have been developed to replace the damaged parts of arteries by atherosclerosis or aneurysm disease of vascular system. Early studies of scaffolds for blood vessel regeneration using tissue engineering were mainly studies of preparing collagens, or biodegradable polymers such as natural polymers or PGA in the tube form; seeding smooth muscle cells or endothelial cells making up vascular tissues thereon followed by culturing them in vitro for a certain period to have some mechanical strength; and then transplanting thereof in vivo.

However, the replacement materials made with the biodegradable polymers had a problem of severe blood-leakage in the early stage of in vivo transplantation because they were prepared by methods preparing porous woven fabrics. In order to compensate the problem, surface treatment studies such as blood clotting on the vessel surface in advance or collagen coating were conducted, but their result were not satisfactory. Further, the blood vessel replacing materials have severe compliance mismatch (elasticity difference) which acts as the major cause of artificial vascular occlusion and fracture. It is known that their compliances are usually one tenth of those of arteries.

Then, as a block copolymer showing biocompatibility and antithrombotic activity at the same time, SPEU (segmented polyether urethane) was used, but it was impossible to use for a long time because it caused calcification when it was transplanted in vivo.

To solve these problems, tissue engineering techniques were developed to make the environment similar with intravascular environment by culturing vascular endothelial cells in an artificial blood vessel.

As conventional biodegradable materials, a tube-type scaffold prepared by winding polyglycolic acid (PGA) nonwoven fabric or poly-L-lactic acid (PLLA) woven fabric to a cylindrical shaft followed by stitching up with a suture to maintain a tube shape like the shape of the blood vessel of a living body, or prepared by soaking a PGA or PLLA mesh to a solution dissolving a polymer showing completely different dissolution property therewith such as poly-L-lactide-co-caprolactone (PLCL) followed by freeze-drying is being used.

Likewise, in case of the tube-type scaffold, a method for forming pores using poly-L-lactide-co-caprolactone (PLCL) by freeze drying is being used, but PGA or PLLA has problems of much lower elasticity than PLCL, difficulty to control degradation rate and the like.

Further, structure of the scaffold such as pore size has a limit to playing a role of an artificial blood vessel without blood-leakage under high pressure. It is preferred that the pore size of the inner part of the artificial scaffold for blood regeneration is small enough to block the blood-leakage through the pores in the blood vessel wall when blood circulates, and the pore size of the outer part thereof is big enough to make cell attachment and proliferation in the blood vessel cure process easy.

In addition, an artificial blood vessel prepared with only PLCL is mainly made by a method such as freeze-drying, casting, extruding and the like, and the made artificial blood vessel has drawbacks of low cell seeding efficiency and mechanical strength.

Therefore, there has been a demand to develop a tissue engineering porous scaffold for an artificial vessel having high elasticity and excellent mechanical strength.

Meanwhile, the electrospinning process is a process to spin a low density polymer into the fiber form in a flash using high-voltage electrostatic force by applying larger electrostatic force than the surface tension in the polymer. Recently, it is used to prepare nanometer-grade fibers, and studies thereof are actively progressing. The nano-fibers can provide various physical properties which can't be obtained from the existing fibers, and a web consisting of the nano-fibers is a membrane-type material having porosity and is very useful to various fields such as filters, wound dressings, artificial scaffolds and the like.

SUMMARY OF THE INVENTION

Accordingly, it is an object of the present invention to provide a method for preparation of an artificial blood vessel using a tube-type porous biodegradable scaffold and a stem cell, which is prepared by electrospinning method, has good mechanical properties such as elasticity and flexibility, and has improved cell-compatibility by having similar structure and shape to biological tissues so as to be used for tissue regeneration therapy.

It is other object of the present invention to provide an artificial blood vessel made by the method of the present invention.

In accordance with one aspect of the present invention, there is provided a method for preparation of an artificial blood vessel using a tube-type porous biodegradable scaffold having a double layered structure and a stem cell, which comprises the following steps of:

a) preparing a tube-type porous biodegradable scaffold having a double layered structure;

b) seeding a stem cell onto the tube-type porous biodegradable scaffold having a double layered structure; and c) applying mechanical stimulus to the stem cell-seeded tube-type porous biodegradable scaffold having a double layered structure.

ADVANTAGEOUS EFFECTS OF THE INVENTION

The present invention has characteristics of enabling a cell to attach thereto easily and promoting cell growth as well as being absorbed to a human body by natural biodegradation by using a tube-type porous biodegradable scaffold having a double layered structure, which comprises an inner membrane forming a membrane structure wherein biodegradable polymer nano-fibers are randomly arranged, and an outer membrane wherein biodegradable polymer nano-fibers are circumferentially arranged; and therefore, it is useful to regenerate damaged tissues.

Further, the stem cell is seeded to the inner membrane and the outer membrane the tube-type porous biodegradable scaffold having a double layered structure, respectively and rotated so as to be stably fixed and to differentiate. In addition, the stem cell differentiates to a vascular endothelial cell at the inner membrane of the tube-type porous biodegradable scaffold having a double layered structure and a smooth muscle cell at the outer membrane thereof by shear stress and tension force, respectively, and therefore, the inner part can prevent blood-leakage through pores in the wall of the blood vessel when blood circulates, and the outer part shows effect that cell attachment and proliferation are easy in the process of blood vessel healing.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Figure 1:
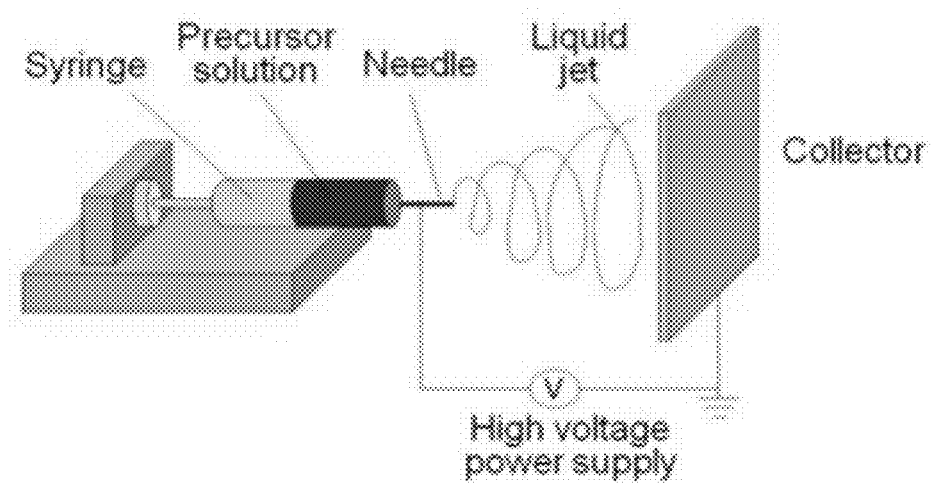
FIG. 1: A schematic diagram of the electrospinning apparatus according to the present invention.

Hereinafter, the method of the present invention for preparation of an artificial blood vessel using a tube-type porous biodegradable scaffold having a double layered structure and a stem cell is described in detail.

First of all, a tube-type porous biodegradable scaffold having a double layered structure is prepared. In the present invention, the tube-type porous biodegradable scaffold having a double layered structure is characterized by comprising an inner membrane forming a membrane structure wherein biodegradable polymer nano-fibers are randomly arranged, and an outer membrane wherein biodegradable polymer nano-fibers are circumferentially arranged.

In the present invention, the structure of the inner and outer membranes of the tube-type porous biodegradable scaffold having a double layered structure is a copy of the biological tissue structure, and it make a stem cell, other cell, a drug and a compound be easily injected, regenerated, adhered and contained to the inside of the scaffold as well as it makes possible to obtain effective and excellent cell regeneration effect and high patency rate by blocking the leak of a blood vessel or compliance mismatch.

In the present invention, the tube-type porous biodegradable scaffold having a double layered structure is characterized by being prepared by electrospinning method comprising the following steps of:

a) forming the inner membrane by electrospinning a solution containing a biodegradable polymer to a rotating mandrel which rotates at a constant speed of v1; and b) forming the outer membrane by changing the rotation speed of the rotating mandrel to v2.

In the present invention, the biodegradable polymer used to prepare the tube-type porous biodegradable scaffold having a double layered structure may be any one of various degradable polymers known in the art used for an artificial scaffold, and preferably, it can be at least one artificial polymer selected from a group consisting of poly(L-lactide-co-ε-caprolactone), polylactic acid (PLA), polyglycolic acid (PGA), poly(D,L-lactide-coglycolide) (PLGA), poly(caprolactone), diol/diacid-based aliphatic polyester, polyester-amide/polyester-urethane, polyethylene oxide, poly(valerolactone), poly(hydroxybutyrate) and poly(hydroxyvalerate), or at least one natural polymer selected from a group consisting of chitosan, chitin, alginic acid, collagen, gelatin and hyaluronic acid.

The poly(L-lactide-co-ε-caprolactone) is more suitable for a scaffold of an artificial tissue than a homopolymer of polycapropactone because it has excellent mechanical properties such as flexibility and elasticity and proper biodegradation period due to its uniformly arranged structure.

Electrospinning is a process to micronized conductive fluid using interaction between electrostatic field and the conductive fluid. When the exterior electrostatic field is applied to the conductive fluid (for example: semi-diluted polymer solution or polymer melt), a suspended conical droplet is formed, and therefore, surface tension of the droplet maintains a balance with electric field. The electrostatic micronization is occurred when the electrostatic field is strong enough to overcome surface tension of liquid. Then, the liquid droplet becomes unstable and very small jet stream is jetted out of the droplet surface. When the jetted material comes to a grounded target material, the material can be collected as an interlinked web containing relatively fine, i.e., small diameter fibers. A film (or membrane) produced from these small diameter fibers has very high surface to volume ratio and small pore size.

FIG. 1 is a diagram of the electrospinning apparatus according to the present invention. A polymer solution (38) containing a biodegradable polymer dissolved in a solvent is held in a syringe. Flow rate may be changed according to the desired physical properties of a polymer scaffold, i.e., membrane thickness, fiber diameter, pore size, membrane density and the like. A syringe pump (32) supplies the polymer solution to a needle (42). The needle (42) has a tip structure which makes possible to form and transmit jet stream without interference. Electric charge of the range of about 10 to about 30 kV is applied to the needle via a wire (41A) by high-voltage power (48). The mandrel (56A) is located to generate electric field between the charged needle (42) and the mandrel (56A). The electric field makes the jet stream of the polymer solution jet out of a spinneret, and makes it be sprayed toward the mandrel (56A) so as to form a filament or fiber (46) of micron or nanometer diameter. The drill chuck is grounded using earth wires (41B and 41C).

In the electrospinning of the present invention, a rotating mandrel is used. The mandrel is mechanically attached to a motor through a drill chuck. The rotating metal mandrel can cause random deposit of the biodegradable polymer nano-fiber on the surface of the mandrel so as to form a tube when the mandrel is removed. The oriented fibers having a layer wherein the biodegradable polymer nano-fibers are uniformly applied are prepared by rotating the mandrel.

The circumferential arrangement of the biodegradable polymer nano-fiber is controlled by changing the mandrel rotation speed. When the mandrel rotates slowly, the biodegradable polymer nano-fibers are longitudinally arranged, and when the mandrel rotation speed increases, the biodegradable polymer nano-fibers are circumferentially arranged. In order to prepare a multi-layered tube-type porous scaffold having each layer of certain arrangement, various mandrels and rotation speeds can be used.

In the present invention, the motor rotates the mandrel at the speed of about 1 rpm to about 500 rpm. The mandrel rotation speed is preferably 200 rpm to about 500 rpm. In other exemplary embodiment, the motor rotation speed is about 1 rpm to about 100 rpm.

In the present invention, to arrange the inner membrane randomly and outer membrane circumferentially, it is preferred that the ratio of the rotation speed of the rotating mandrel, v1 in the step of forming the inner membrane and the rotation speed of the rotating mandrel, v2 in the step of forming the outer membrane is 1:10 to 1:11.

Further, when the inner membrane and the outer membrane are formed with poly(L-lactide-co-ε-caprolactone), respectively, the rotation speed of the rotating mandrel is preferably 0.2 to 0.4 m/s in the step of forming the inner membrane, and the rotation speed of the rotating mandrel is preferably 3 to 4 m/s in the step of forming the outer membrane.

In the present invention, when the inner membrane is formed, polyethyleneoxide is firstly spun for 5 to 15 min, and then poly(L-lactide-co-ε-caprolactone) is spun, preferably. In applying the artificial scaffold to a large-diameter blood vessel, proteins and platelets in blood are hardly adsorbed or attached to the inner surface of the artificial scaffold due to high blood circulation rate, but in applying it to a small-diameter blood vessel, various proteins and platelets are adsorbed or attached to the inner surface of the artificial scaffold due to low blood circulation rate. In order to improve the problem, polyethyleneoxide known as a polymer minimizing the attachment of a protein and a cell was spun in advance to locate the polymer at the innermost part of the inner membrane, so as to inhibit the attachment of a protein and a platelet and to increase patency rate of the artificial scaffold. Further, when polyethyleneoxide is firstly spun in the preparation process, poly(L-lactide-co-ε-caprolactone) can be easily separated from the mandrel.

Electrospinning to make other biodegradable polymer nano-fibers can be conducted according to methods using known devices. When more polar solution is used to prepare a biodegradable polymer solution, average fiber diameter tends to be reduced according to the increase of distance between the needle and the mandrel. The scaffold diameter is also reduced even when voltage of the device and the polymer concentration increase.

In the present invention, the electrospinning is conducted under the condition of spin distance of 200 to 220 nm and voltage between the needle for spin and the rotating mandrel of 12 to 20 KV, and 14 to 16 KV, preferably.

Then, stem cells are seeded onto the tube-type porous biodegradable scaffold having a double layered structure prepared as described above.

In the present invention, the stem cells, which can be seeded onto the tube-type porous biodegradable scaffold having a double layered structure, can be selected from a group consisting of mesenchymal stem cells, hematopoietic stem cells, fetal cell-derived stem cells, adipose-derived stem cells, umbilical cord blood stem cells, hemangioblast, vascular endothelial cells, vascular smooth muscle cells, hematopoietic stem cells and embryonic stem cells, preferably.

Specifically, the step of seeding the stem cells to the tube-type porous biodegradable scaffold having a double layered structure comprises the following steps of:

a) suspending the stem cells into an endothelial cell culture solution, and seeding the cell culture solution containing the stem cells onto the inner membrane of the tube-type porous biodegradable scaffold having a double layered structure;

b) fixing the stem cells to the inner membrane of the tube-type porous biodegradable scaffold having a double layered structure by rotating the tube-type porous biodegradable scaffold having a double layered structure of step a) at the speed of 0.5 to 5 rpm for 1 to 6 hours;

c) suspending the stem cells into the culture solution, and seeding the culture solution containing the stem cells onto the outer membrane of the tube-type porous biodegradable scaffold having a double layered structure of step b); and d) fixing the stem cells to the outer membrane of the tube-type porous biodegradable scaffold having a double layered structure by rotating the tube-type porous biodegradable scaffold having a double layered structure of step c) at the speed of 0.5 to 5 rpm for 15 to 30 hours.

In the present invention, the step of seeding the stem cells onto the tube-type porous biodegradable scaffold having a double layered structure is characterized that the stem cells are seeded onto the inner side and the outer side of the tube-type porous biodegradable scaffold having a double layered structure, respectively, the seeded stem cells are also cultured inside of the tube-type porous biodegradable scaffold having a double layered structure, and the tube-type porous biodegradable scaffold having a double layered structure is rotated in order to fix the stem cells to the scaffold.

Figure 2:
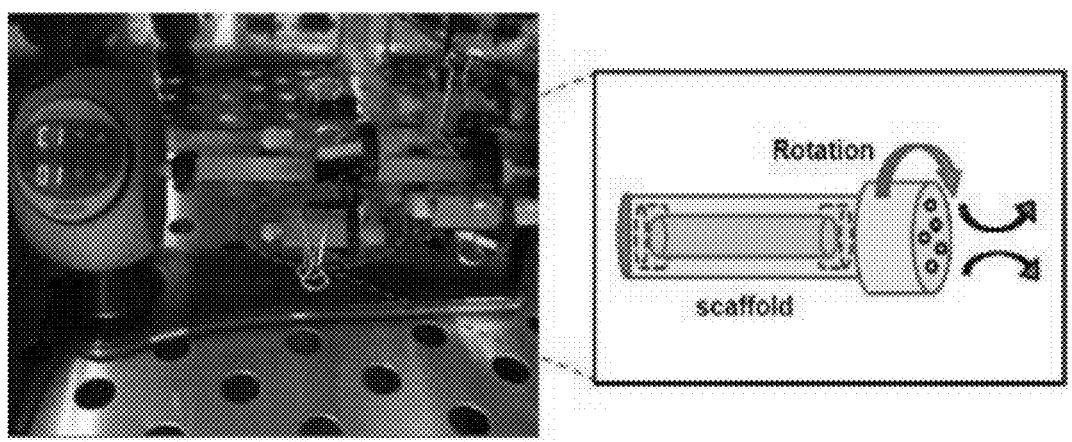
FIG. 2: An image and schematic diagram of the system used to rotate the tube-type porous biodegradable scaffold having a double layered structure in the present invention.

The method to rotate the tube-type porous biodegradable scaffold having a double layered structure is not particularly limited, and any method known to the person skilled in the art can be used as the method. The method to rotate the tube-type porous biodegradable scaffold having a double layered structure used in the present invention is briefly represented in FIG. 2. As shown in FIG. 2. The stem cells can be fixed to the inside of the scaffold by immersing the tube-type porous biodegradable scaffold having a double layered structure of the present invention into a test tube containing the culture solution to be fixed followed by adding a medium containing cells, and by rotating the test tube.

Further, in the present invention, the culture solution can comprise at least one selected from a group consisting of vascular endothelial growth factor, fibroblast growth factor, nerve growth factor, platelet-derived growth factor, smooth muscle cell growth factor, heparin, thrombin, laminin, fibronectin and collagen, preferably.

Further, in the present invention, the culture solutions for the inside and outside of the tube-type porous biodegradable scaffold having a double layered structure can be different in order to differentiate the seeded stem cells to vascular endothelial cells to the inside of the tube-type porous biodegradable scaffold having a double layered structure and to smooth muscle cells to the outside thereof. Namely, a vascular endothelial growth factor-added culture solution is used for the inside of the tube-type porous biodegradable scaffold having a double layered structure, and a smooth muscle cell growth factor-added culture solution is used for the outside thereof.

In the method of the present invention for preparation of an artificial blood vessel using a tube-type porous biodegradable scaffold having a double layered structure and a stem cell, mechanical stimulus is next applied to the stem cell-seeded tube-type porous biodegradable scaffold having a double layered structure so as to accelerate the stem cell differentiation.

The present invention is characterized by comprising a step of applying shear stress and tension force as mechanical stimulus to the stem cell-seeded tube-type porous biodegradable scaffold having a double layered structure, and specifically, the step of applying the mechanical stimulus comprises the following steps of:

a) applying shear stress to the stem cell-seeded tube-type porous biodegradable scaffold having a double layered structure; and b) applying tension force to the stem cell-seeded tube-type porous biodegradable scaffold having a double layered structure.

In the present invention, the method to apply shear stress and tension force to the stem cell-seeded tube-type porous biodegradable scaffold having a double layered structure is not particularly limited, and any method generally known to the person skilled in the art can be used as the method.

Specifically, to apply the shear stress, the stem cell-seeded tube-type porous biodegradable scaffold having a double layered structure is immersed into the cell culture solution, and the shear stress of 2 dyne/cm$^2$ to 5 dyne/cm$^2$ per unit area of the stem cell-seeded tube-type porous biodegradable scaffold having a double layered structure for 20 to 30 hours by flow of the endothelial cell culture solution, preferably.

Further, in the step of applying tension force, the second tension force of more than the first tension force is prefer-ably applied after applying the first tension force, and it is preferred to apply tension force of 3% to 5%.

The present invention further provides an artificial blood vessel made by the preparation method of the present invention. The artificial blood vessel of the present invention is characterized by having diameter of 2 mm to 5 mm.

The artificial blood vessel prepared according to the preparation method of the present invention is characterized by comprising vascular endothelial cells differentiated from mesenchymal stem cells at the inner membrane, and smooth muscle cells differentiated from mesenchymal stem cells at the outer membrane.

The following Examples are intended to illustrate the present invention without limiting its scope.

EXAMPLE 1

Preparation of Tube-type Porous Biodegradable Scaffold Having a Double Layered Structure The electrospinning system consists of a high-voltage power supply (SHV200RD-40K, ConverTesh Co,. Ltd.), a syringe pump (KDS100, KD Scientific), a syringe, a 18G needle, CAM operating the needle up and down, and 5 mandrels. The rotating mandrel was operated using servo-motor system.

Electrospinning condition to form random arrangement of an inner membrane is as follows. Electrospinning distance was 220 nm, rotation speed of the rotating mandrel was 0.3 m/s, voltage of the needle electrospinning polyethyleneoxide was 14 KV, and voltage of the needle electrospinning poly(L-lactide-co-ε-caprolactone) was 16 KV. Concentration of polyethyleneoxide inserted to the needle was 30% (w/v) and supply rate thereof was 2 ml/h, and concentration of poly(L-lactide-co-ε-caprolactone) was 13% (w/v) and supply rate thereof was 1.7 ml/h.

First of all, polyethyleneoxide (PEO, MW: 100,000) was dissolved in distilled water to obtain 30% (w/v) polyethyl-eneoxide solution, and the polyethyleneoxide solution was put into an electrospinning needle. Electrospinning to the mandrel rotating at 0.3 m/s was performed for 10 min according to the above condition.

Then, poly(L-lactide-co-ε-caprolactone) (50:50, MW: 125 kDa) was dissolved in distilled water to obtain 13% (w/v) poly(L-lactide-co-ε-caprolactone) solution, and the solution was inserted to an electrospinning needle. The poly(L-lactide-co-ε-caprolactone) solution inserted to the needle was spun onto the spun polyethyleneoxide solution which was rotating at 0.3 m/s for 2 hours to prepare an inner membrane. Then, the rotation speed of the rotating mandrel was accelerated to 3.14 m/s, and the spinning was conducted for 1 hour to prepare an outer membrane continuously linked to the inner membrane.

Figure 3:
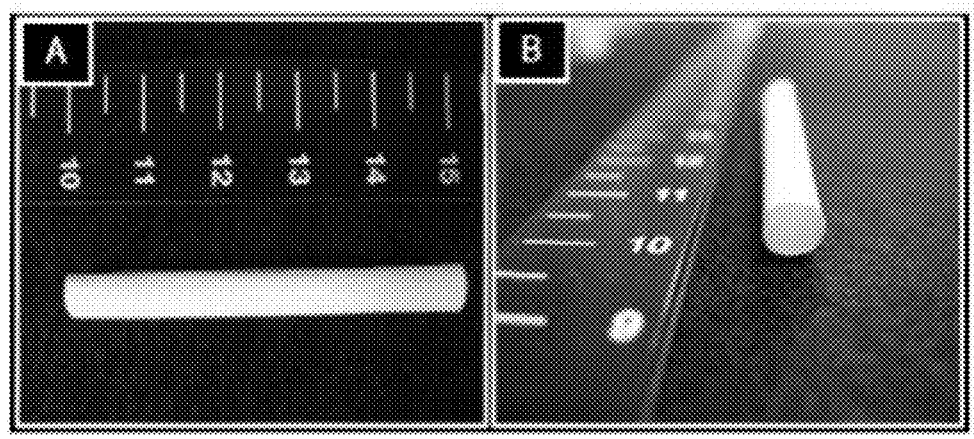
FIG. 3: Images showing the size of the tube-type porous biodegradable scaffold having a double layered structure.
Figure 4:
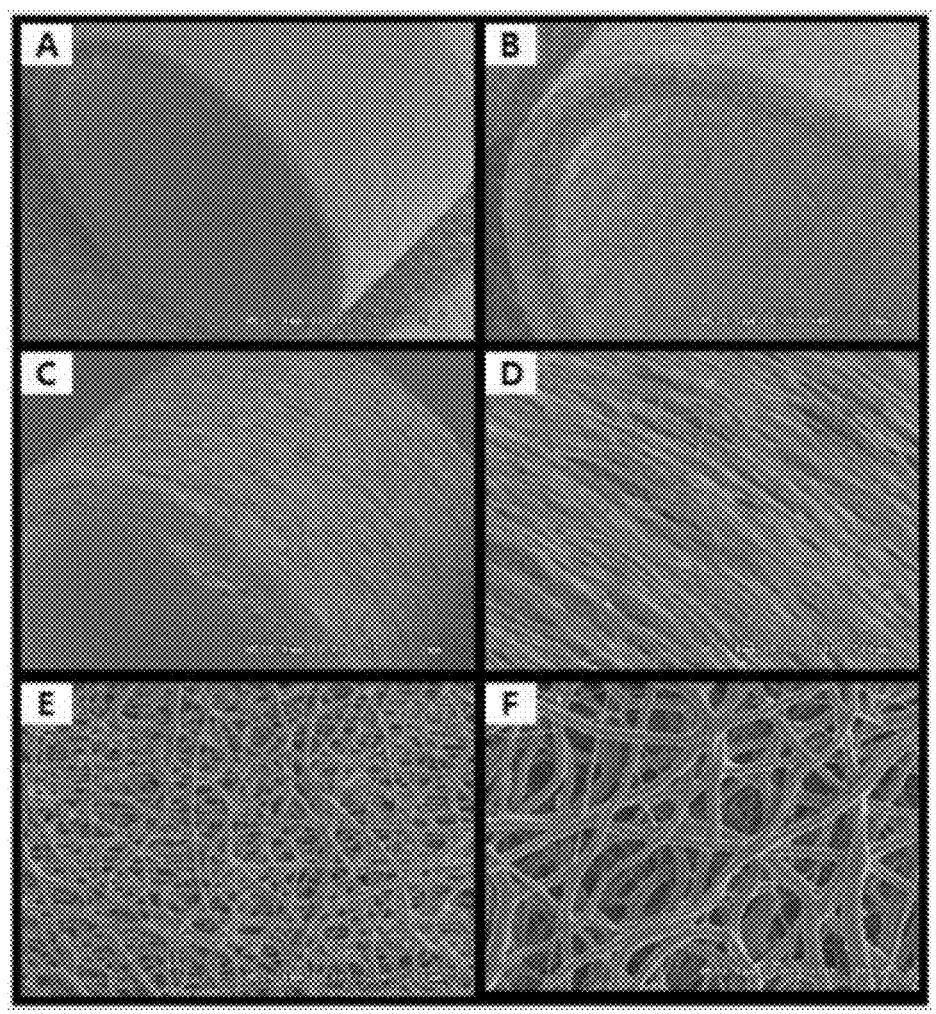
FIG. 4: SEM images of the tube-type porous biodegradable scaffold having a double layered structure.

An image representing size of the tube-type porous biodegradable scaffold having a double layered structure is in FIG. 3, and an SEM image of the tube-type porous biodegradable scaffold having a double layered structure is in FIG. 4. It was confirmed that length of the prepared scaffold is 5 cm as shown in FIG. 3, and PLCL arrangements of the inside and outside of the tube-type porous biodegradable scaffold having a double layered structure are different each other as shown in FIG. 4.

TEST EXAMPLE 1

Figure 5:
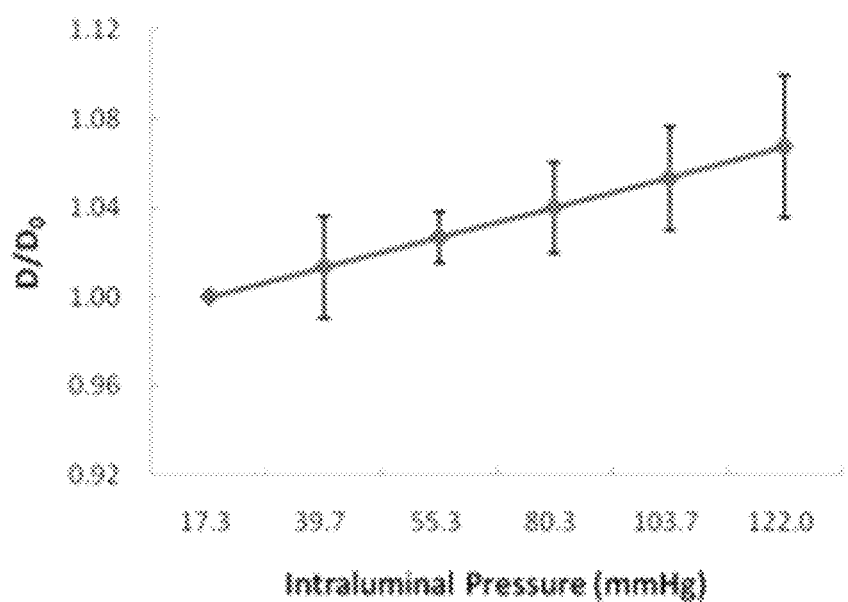
FIG. 5: Results of measuring diameter increase rate of the tube-type porous biodegradable scaffold having a double layered structure prepared in one embodiment of the present invention with increasing internal pressure.

Measuring Elasticity of Tube-type Porous Biodegradable Scaffold Having a Double Layered Structure In order to test elasticity of the tube-type porous biode-gradable scaffold having a double layered structure according to the present invention to the pressure which acts thereon in a blood vessel, the increase rate of diameter of the tube-type porous biodegradable scaffold having a double layered structure prepared in Example 1 was measured while increasing and applying the pressure to the inside of the scaffold, and the results are shown in FIG. 5.

As shown in FIG. 5, it was confirmed that the diameter of the tube-type porous biodegradable scaffold having a double layered structure was increased in proportion to the pressure until the pressure of 122 mmHg was applied thereto, and therefore the scaffold exhibited high elasticity.

EXAMPLE 2

Figure 6:
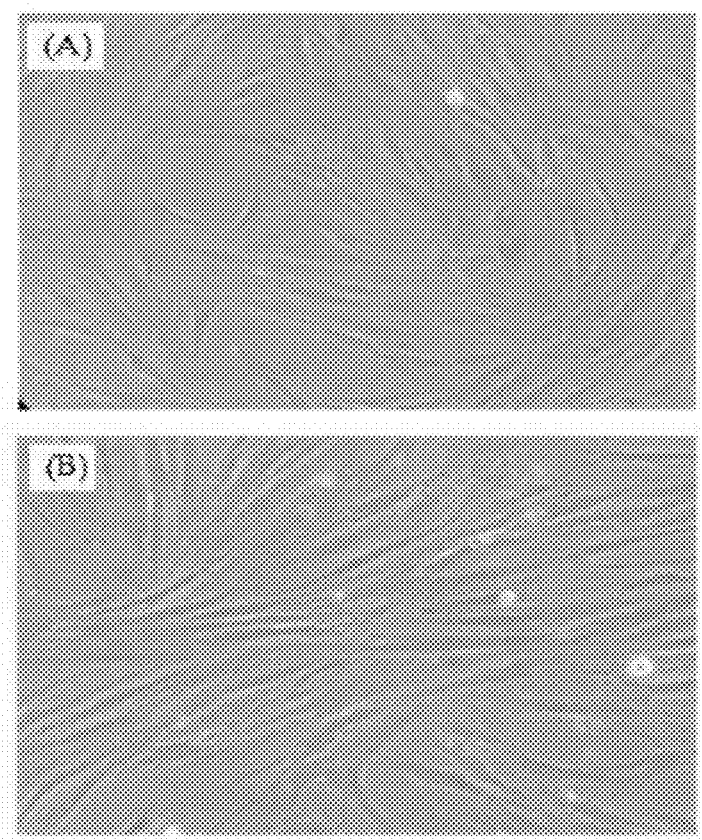
FIG. 6: Images of the cultured mesenchymal stem cells.

Seeding Mesenchymal Stem Cell onto Tube-type Porous Biodegradable Scaffold Having a Double Layered Structure Mesenchymal stem cells purchased from Lonza Walersville were cultured in MSC growth medium BulletKit (PT-3001, Lonza), and an image of the cultured mesenchymal stem cells was shown in FIG. 6.

The tube-type porous biodegradable scaffold having a double layered structure prepared in Example 1 was sterilized by decreasing alcohol concentration. Then, it was pre-warmed in the culture medium for 4 hours, and the surface thereof was coated with fibronectin of 8 μg/cm$^2$.

The mesenchymal stem cells of passage 5 were suspended in EGM-2 medium (Lonza) and seeded onto the lumen of the tube-type porous biodegradable scaffold having a double layered structure prepared in Example 1.

The mesenchymal stem cells of passage 5 were suspended in SGM-2 medium (Invitrogen, Carlsbad, Calif.), and then seeded onto the outer membrane of the tube-type porous biodegradable scaffold having a double layered structure prepared in Example 1 at a concentration of 5×10$^5$ cells/cm$^2$. Specifically, the endothelial cell growth medium (EGM-2) and the smooth muscle cell growth medium (SGM-2) comprise following components.

| endothelial cell growth medium (EGM-2) | smooth muscle cell growth medium (SGM-2) |
|---|---|
| No BBE (Bovine Brain Extract) | hEGF |
| hEGF | Insulin |
| Hydrocortisone | hFGF-B |
| GA-1000 (Gentamicin Amphotericin-B) | FBS |
| FBS (Fetal Bovine Serum) 10 ml | Gentamicin/Amphotericin-B |
| VEGF | |
| hFGF-B | |
| R3-IGF-1 | |
| Ascorbic Acid | |
| Heparin | |

Then, they were rotated by the system shown in FIG. 2 at 1 rpm for 24 hours.

EXAMPLE 3

Applying Shear Stress

Figure 7:
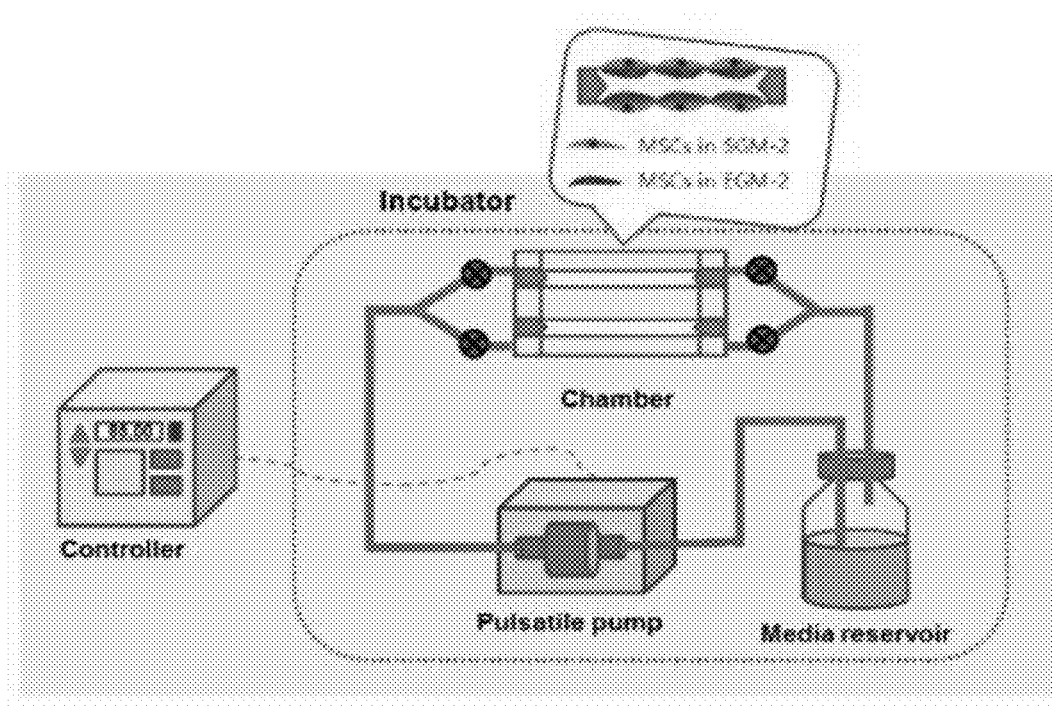
FIG. 7: A schematic diagram of the system applying shear stress to the tube-type porous biodegradable scaffold having a double layered structure according to one embodiment of the present invention.

In order to apply mechanical stimulus to the mesenchymal stem cell-seeded tube-type porous biodegradable scaffold having a double layered structure of Example 2, the system illustrated in FIG. 7 was formed.

Firstly, in order to apply shear stress, as shown in FIG. 7, the mesenchymal stem cell-seeded tube-type porous biodegradable scaffold having a double layered structure of Example 2 was immersed in a culture solution in a chamber, and a pulsatile pump was connected to the culture solution to induce flow of the culture solution in the chamber, and then, two different shear stress of 2.5 dyne/cm$^2$ and 10 dyne/cm$^2$ were applied to the mesenchymal stem cells seeded to the tube-type porous biodegradable scaffold having a double layered structure of Example 2, respectively. As a comparative Example, the mesenchymal stem cells were culture in a medium without applying shear stress.

TEST EXAMPLE 2

Measuring Differentiation Degree of Stem Cell 2-1. Confirmation by RT-PCR

In order to confirm whether the mesenchymal stem cells cultured by applying shear stress of 2.5 dyne/cm$^2$ and 10 dyne/cm$^2$ and the mesenchymal stem cells cultured without applying shear stress as a Comparative Example in Example differentiated to EC and SMC, or not, the expression of the vascular endothelial cell- and the smooth muscle cell-specific marker genes were detected by RT-PCR.

The gene expression was analyzed by extracting total RNA from the cells followed by synthesizing cDNA using reverse transcriptase, and by performing PCR (polymerase-chain reaction) using gene-specific primers.

Figure 8:
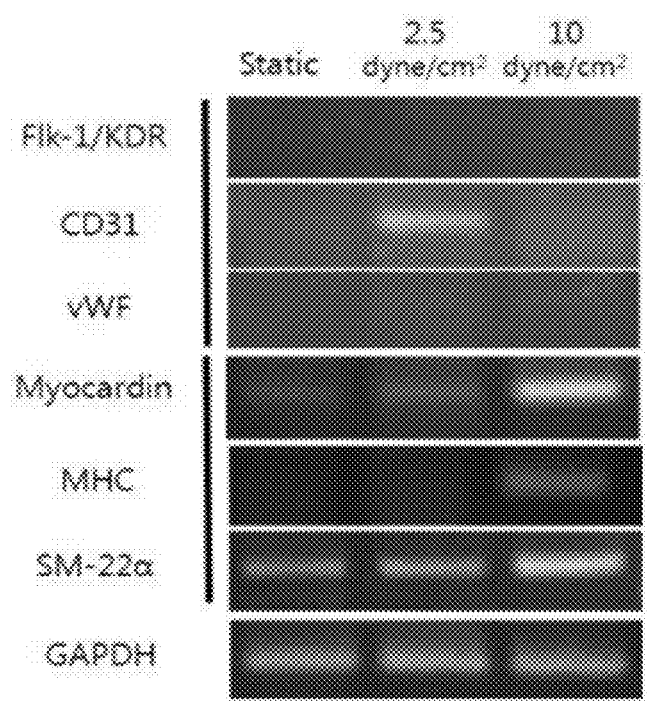
FIG. 8: RT-PCR results of measuring the degree of differentiation of the stem cells according to applying shear stress.

Consequently, as shown in FIG. 8, the expression of CD31 (vascular endothelial cell-specific marker) increased when shear stress of 2.5 dyne/cm$^2$ was applied, and the expressions of myocardin and MHC (smooth muscle cell-specific markers) increased when shear stress of 10 dyne/cm$^2$ was applied.

2-2. Confirmation by immunofluorescence Staining

In order to confirm whether the stem cells differentiated to the vascular endothelial cells and the smooth muscle cells, or not at protein level, the expression of the vascular endothelial cell- and the smooth muscle cell-specific marker were detected by immunofluorescence staining.

In order to stain the mesenchymal stem cells which differentiated to the vascular endothelial cells and the smooth muscle cells with the vascular endothelial cell- and the smooth muscle cell-specific marker, first of all, the culture cells of Example 2 was fixed with 4% paraformaldehyde at a room temperature for 20 min, treated in 0.2% triton X-100 for 10 min for cell membrane permeabilization, and then washed three times with PBST solution (PBS with 0.1% Tween-20) for 5 min each.

Then, a permeabilization solution (PBS with 0.1% Triton X-100) was added to the culture dish and stored at a room temperature for 15 min to deliver antibodies to nucleus by permeabilizing the cells. After 15 min, the permeabilization solution was removed, and blocking was performed with 4% FBS (Fetal Bovine Serum) at a room temperature for 1 hour. And then, a-smooth muscle actin (α-SMA), Calponin (Sigma-Aldrich), von Willebrand Factor (vWF) and Flk-1/KDR (Santa Cruz Biotechnology Inc., Santa Cruz, Calif., USA) antibodies were diluted with a blocking solution followed by adding to the culture dish and stored at 4° C. for 1 day. Next day, to confirm the expressions of the makers with the naked eye using a fluorescence microscope, the secondary antibodies (FITC (1:50)- or TRITC (1:200)-conjugated antibodies) to the primary antibodies of the markers were conjugated to the primary antibodies, and stored at a room temperature for 1 hour. After 1 hour, the culture dish was washed five times with PBST solution for 10 min each, and the expressions of the markers were detected by the fluorescence microscope.

Figure 9:
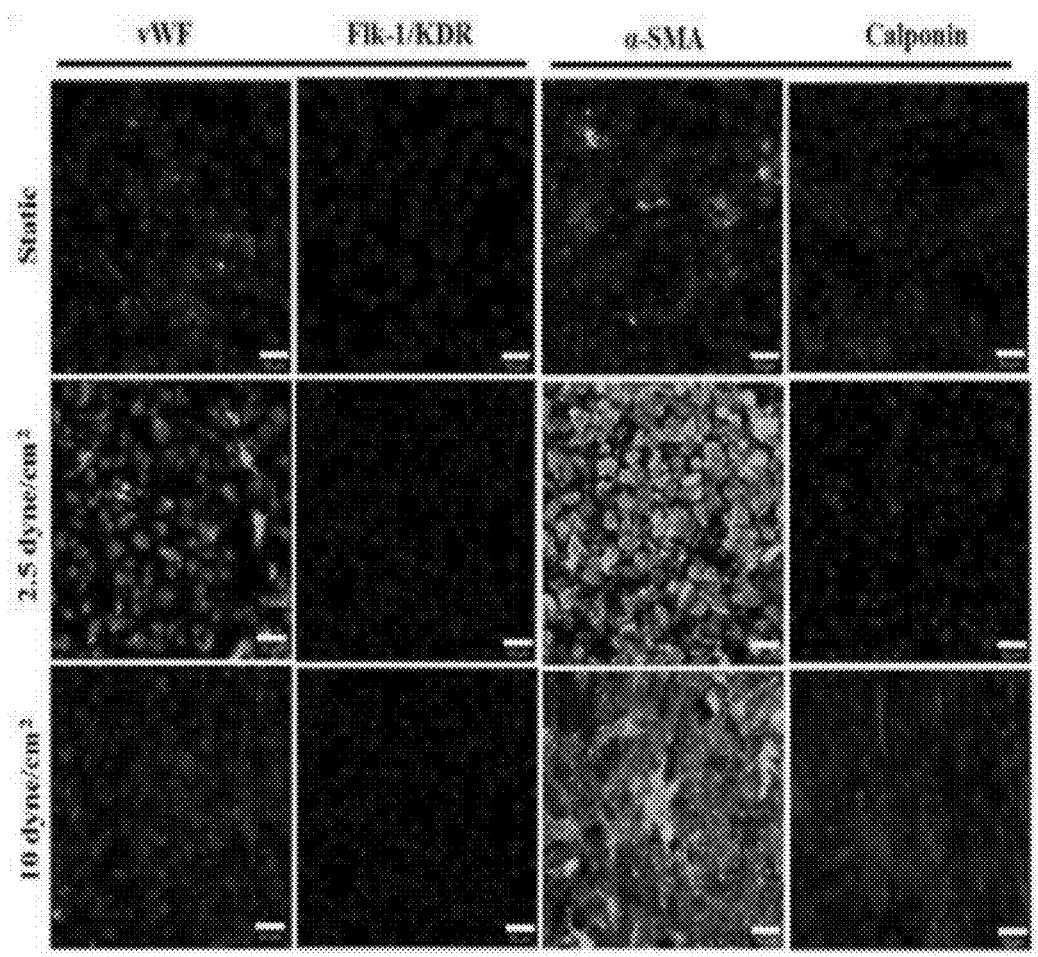
FIG. 9: Immunofluorescence staining results of measuring the degree of differentiation of the stem cells according to time applying shear stress.

Consequently, as shown in FIG. 9, the expression of vWF (vascular endothelial cell-specific marker) increased when shear stress of 2.5 dyne/cm² was applied.

2-3. Confirmation of Expression According to Time Applying Shear Stress

Figure 10:
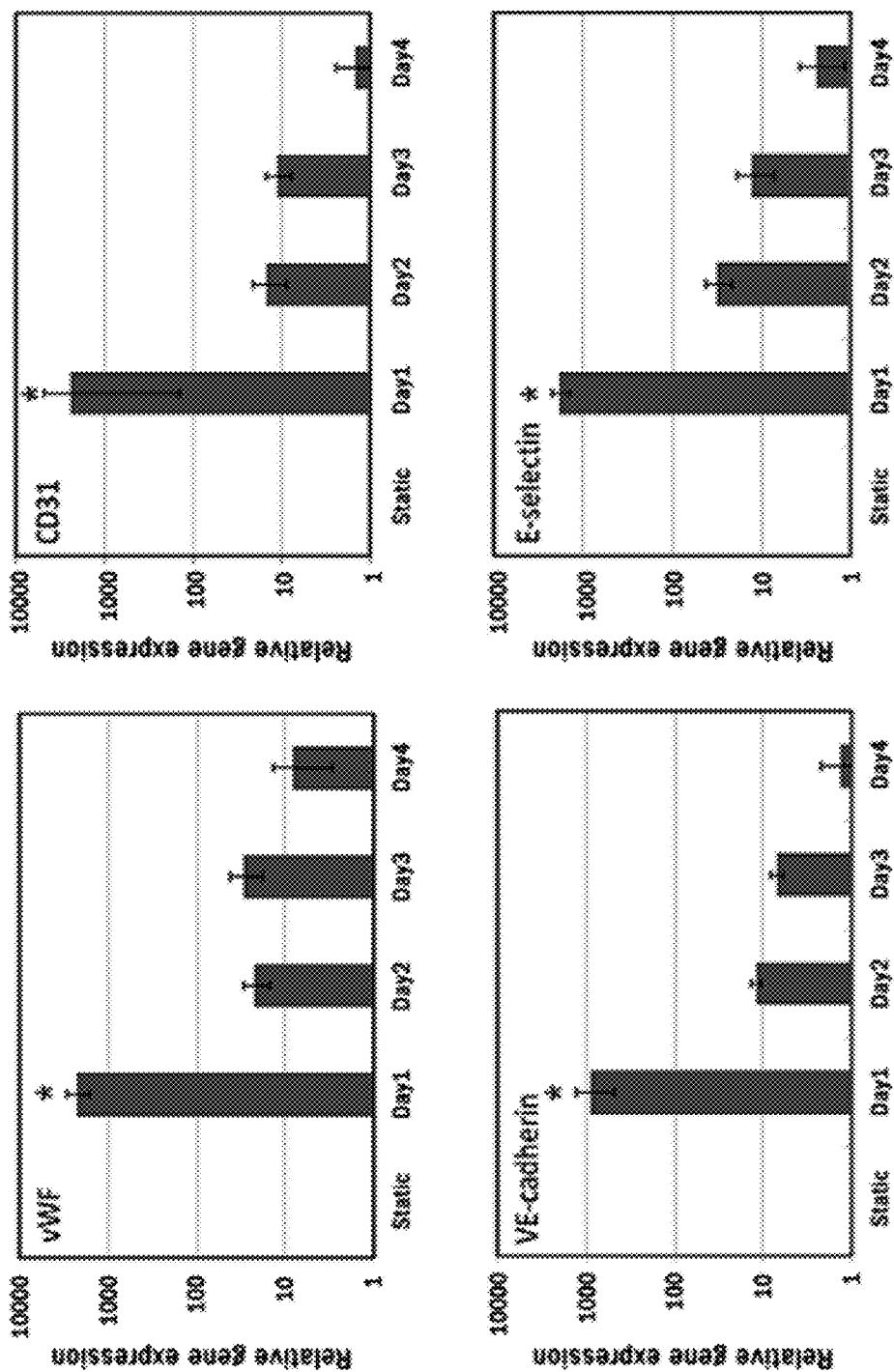
FIGS. 10 and 11: RT-PCR results of measuring the degree of differentiation of the stem cells according to time applying shear stress.
Figure 11:
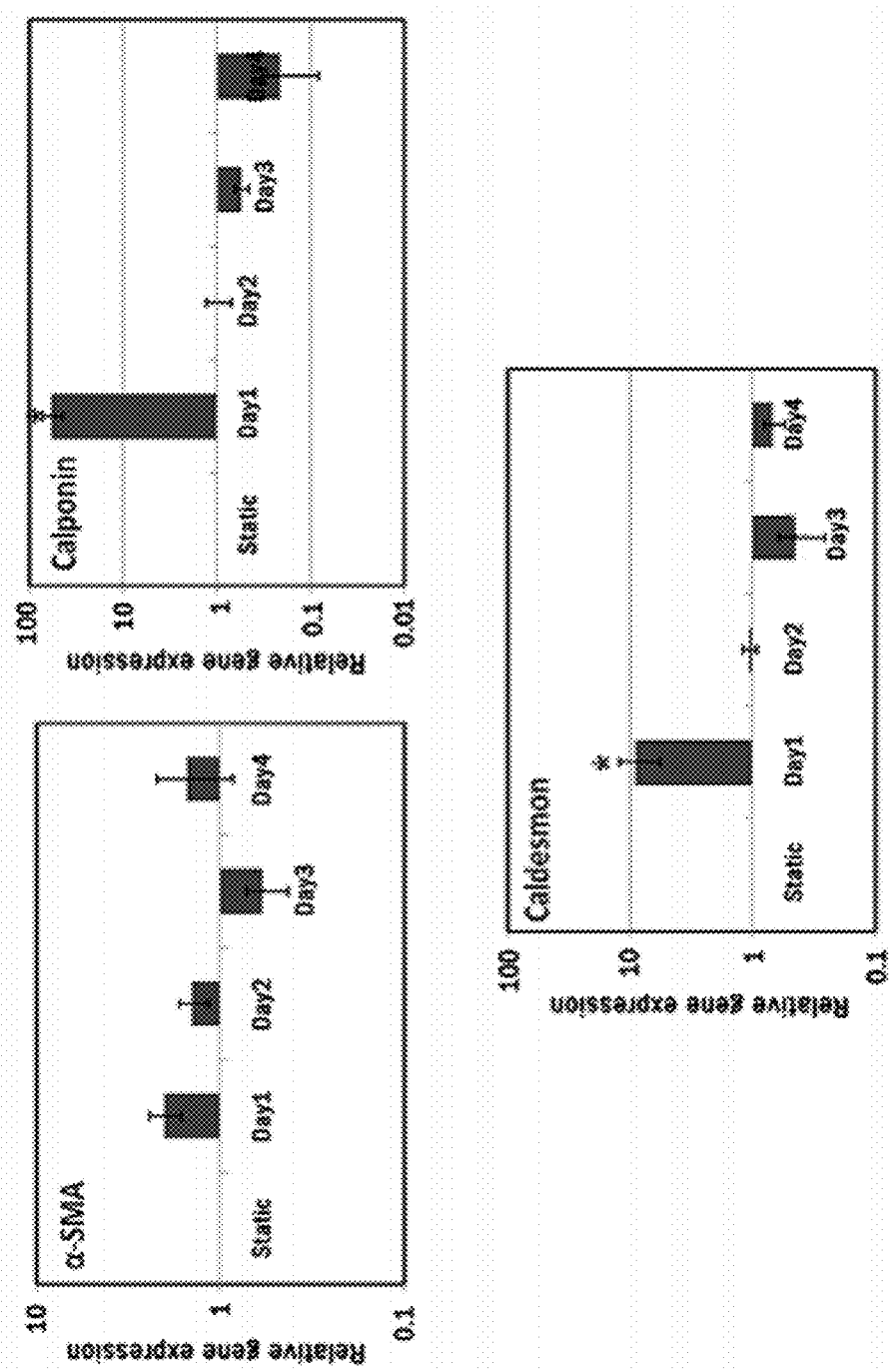

When shear stress of 2.5 dyne/cm² was applied, the expressions of the vascular endothelial cell-specific markers (vWF, CD31, VE-cadherin and E-selectin) and the smooth muscle cell-specific markers (a-SMA, Calponin and Caldesmon) according to time applying shear stress were measured, and the results were shown FIGS. 10 and 11, respectively.

In FIGS. 10 and 11, it was confirmed that the expressions of the endothelial cell-specific markers and the smooth muscle cell-specific markers were highest when shear stress was applied for 24 hours.

EXAMPLE 4

Applying Tension Force

Next, the expressions of the mesenchymal stem cell cultured under the condition of applying shear stress in Example 3 to the vascular endothelial cells and the smooth muscle cells while periodically applying tension force were measured.

The tension force was applied under the condition of fixing both ends of the tube-type porous biodegradable scaffold having a double layered structure of the system shown in FIG. 7. As an Example, 5% tension force was periodically applied for 1 day after periodically applying 3% tension force for 3 days, and as a Comparative Example, tension force was not applied.

TEST EXAMPLE 3

Measuring Differentiation Degree of Stem Cell 3-1. Confirmation by RT-PCR

In order to confirm whether the mesenchymal stem cells cultured by periodically applying 5% tension force for 1 day after periodically applying 3% tension force for 3 days and the mesenchymal stem cells cultured without applying tension force differentiated to EC and SMC, or not, respectively, the expression of the vascular endothelial cell- and the smooth muscle cell-specific marker genes were detected by RT-PCR as described in Test Example 2.

Figure 12:
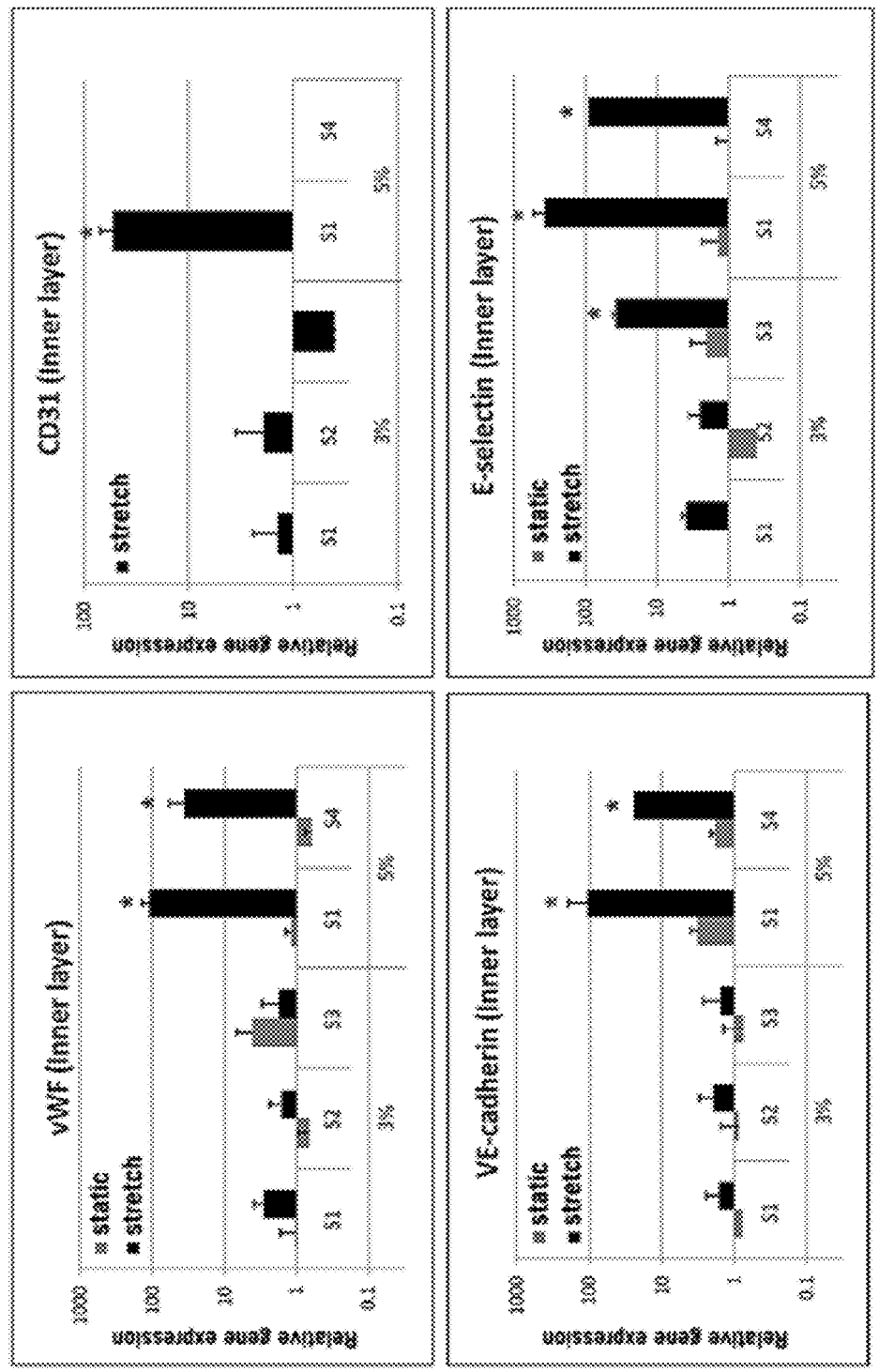
FIGS. 12 and 13: RT-PCR results of measuring the degree of differentiation of the inner membrane stem cells of the tube-type porous biodegradable scaffold having a double layered structure according to applying tension force.
Figure 13:
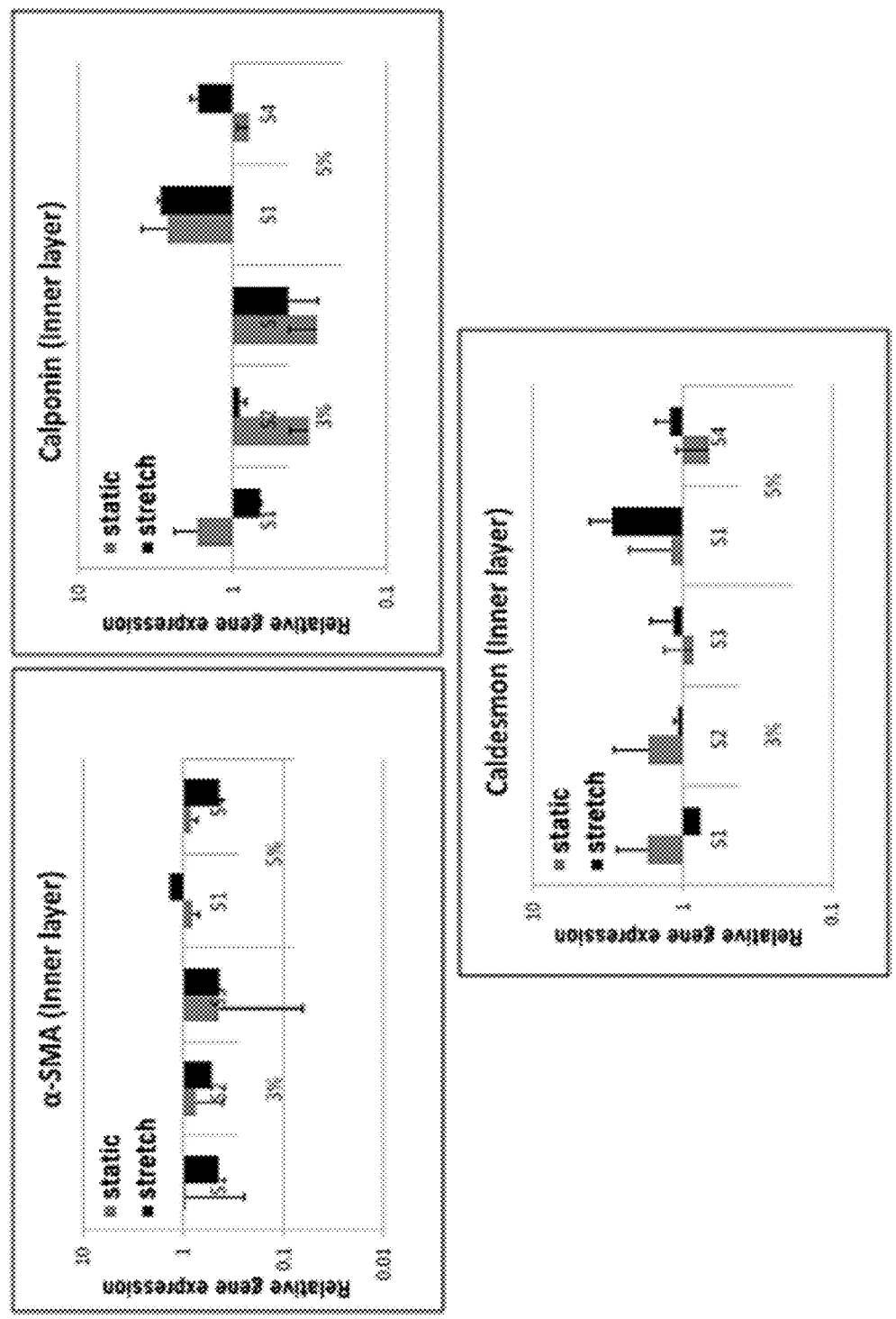

The results of measuring the expressions of the vascular endothelial cell-specific markers (vWF, CD31, VE-cadherin and E-selectin) in the inner membrane cells of the tube-type porous biodegradable scaffold having a double layered structure were shown in FIG. 12, and the results for the smooth muscle cell-specific markers (a-SMA, Calponin and Caldesmon) were shown in FIG. 13.

As shown in FIG. 12, the expressions of the vascular endothelial cell-specific markers (vWF, CD31, VE-cadherin and E-selectin) in the inner membrane of the mesenchymal stem cells increased dramatically when 5% tension force was additionally applied after applying 3% tension force than when only 3% tension force was applied.

Further, as shown in FIG. 13, the expressions of the smooth muscle cell-specific markers (a-SMA, Calponin and Caldesmon) in the outer membrane of the mesenchymal stem cells increased largely when 5% tension force was additionally applied after applying 3% tension force than when only 3% tension force was applied.

Figure 14:
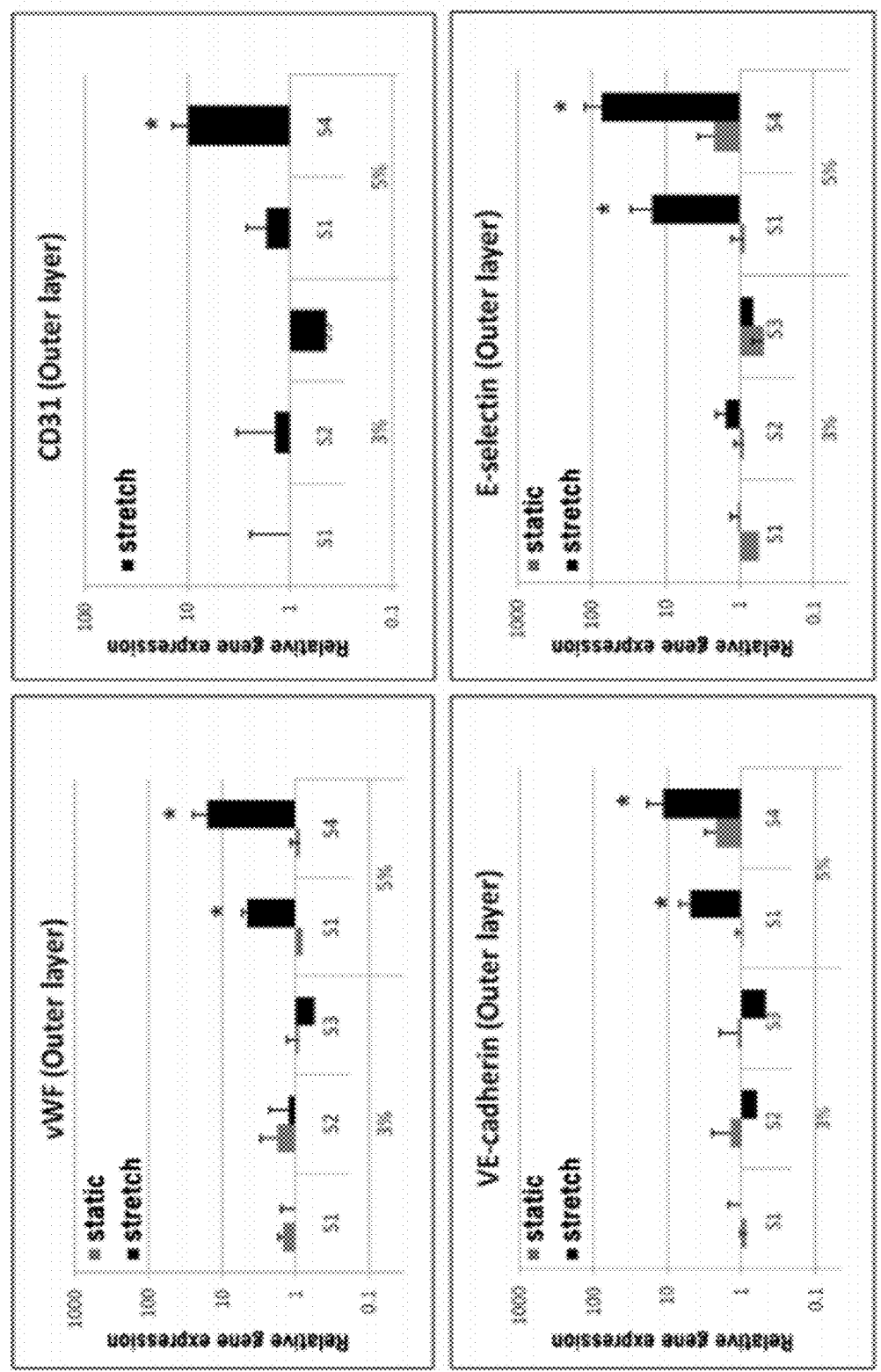
FIGS. 14 and 15: RT-PCR results of measuring the degree of differentiation of the outer membrane stem cells of the tube-type porous biodegradable scaffold having a double layered structure according to applying tension force.
Figure 15:
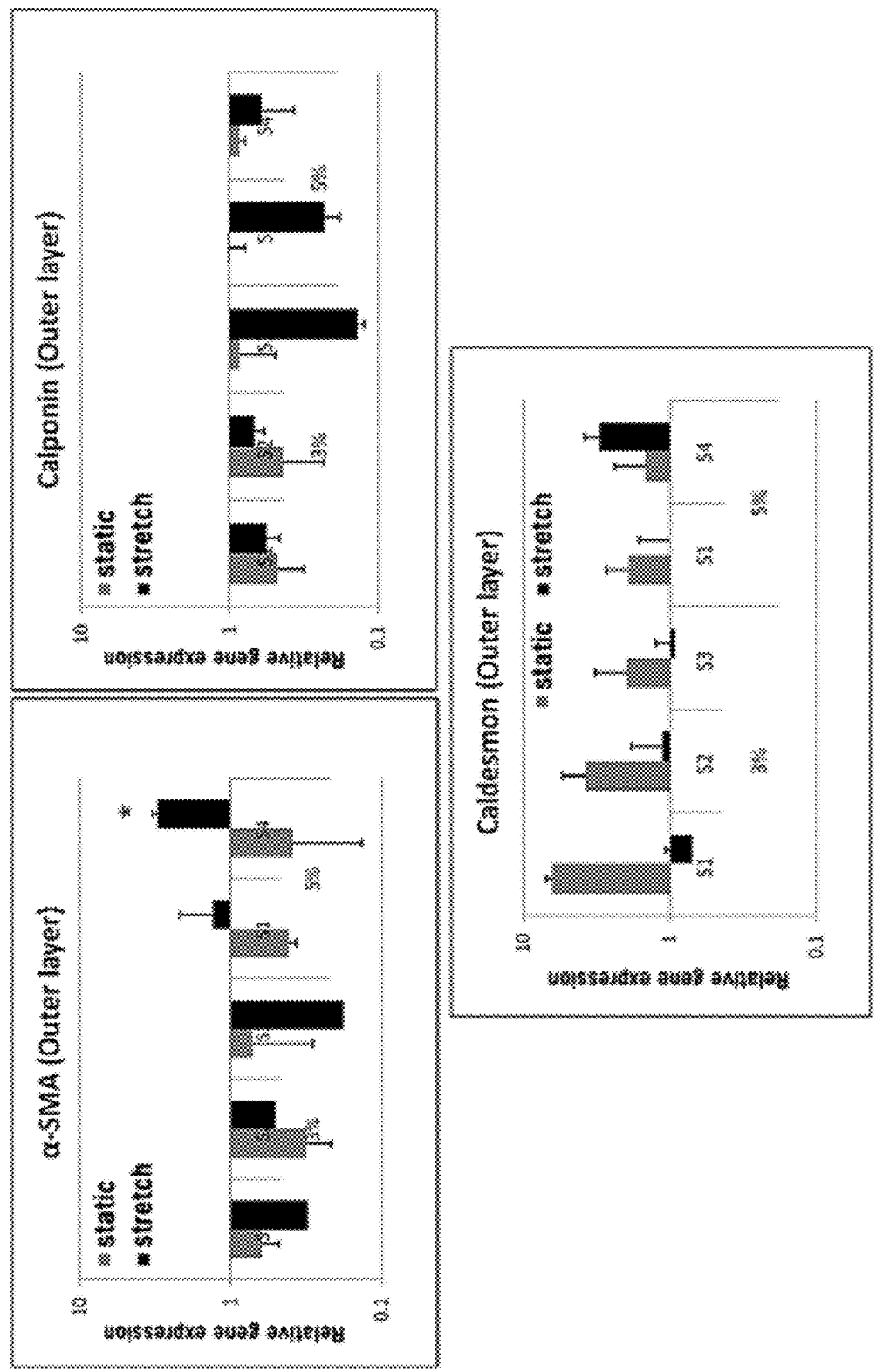

The results of measuring the expressions of the vascular endothelial cell-specific markers and the smooth muscle cell-specific markers in the outer membrane cells of the tube-type porous biodegradable scaffold having a double layered structure were shown in FIGS. 14 and 15, respectively.

As shown in FIG. 14, the expressions of the vascular endothelial cell-specific markers (vWF, CD31, VE-cadherin and E-selectin) in the outer membrane of the mesenchymal stem cells increased dramatically when 5% tension force was additionally applied after applying 3% tension force than when only 3% tension force was applied.

Further, as shown in FIG. 15, the expressions of the smooth muscle cell-specific markers (a-SMA, Calponin and Caldesmon) in the outer membrane of the mesenchymal stem cells increased largely when 5% tension force was additionally applied after applying 3% tension force than when only 3% tension force was applied.

Particularly, when 5% tension force was additionally applied, the expression of the smooth muscle cell-specific markers (a-SMA, Calponin and Caldesmon) in the outer membrane cells increased most largely.

While the invention has been described with respect to the above specific embodiments, it should be recognized that various modifications and changes may be made and also fall within the scope of the invention as defined by the claims that follow.

What is claimed is:

1. A method of preparing an artificial blood vessel comprising:
 a) preparing a tube-type porous biodegradable scaffold having a triple layered structure, wherein the tube-type porous biodegradable scaffold having a triple layered structure comprises an inner layer wherein biodegradable polymer nano-fibers are randomly arranged, an intermediate layer wherein biodegradable polymer nano-fibers are randomly arranged, and an outer layer wherein biodegradable polymer nano-fibers are circumferentially arranged, and the tube-type porous biodegradable scaffold having a triple layered structure is prepared by,
  (i) forming the inner layer by electrospinning a solution containing polyethylene oxide as a biodegradable polymer to a mandrel rotating at a speed of 0.2-0.3 m/s;
  (ii) forming the intermediate layer by electrospinning a solution containing poly(L-lactide-co-ϵ-caprolactone) as a biodegradable polymer to the mandrel rotating at a speed of 0.2-0.3 m/s; and
  (iii) forming the outer layer by electrospinning a solution containing poly(L-lactide-co-ϵ-caprolactone) as a biodegradable polymer to the mandrel rotating at a speed of 3-4 m/s;
 b) seeding mesenchymal stem cells onto the inner layer and outer layer, respectively, of the tube-type porous biodegradable scaffold having a triple layered structure;
 c) applying mechanical stimulus to the stem cell-seeded tube-type porous biodegradable scaffold having a triple layered structure by:
  (1) applying a sheer stress to the mesenchymal stem cell-seeded tube-type porous biodegradable scaffold having a triple layered structure such that differentiation of the mesenchymal stem cells occurs; and
  (2) applying a 3-5% strain to the mesenchymal stem-cell seeded tube-type porous biodegradable scaffold length having a triple layered structure, wherein the step of applying a tension force comprises a first tension force and a second tension force and the second tension force is greater than the first tension force; and d) forming the artificial blood vessel which comprises vascular endothelial cells differentiated from mesenchymal stem cells at the inner layer surface and smooth muscle cells differentiated from mesenchymal stem cells at the outer layer surface.

2. The method of claim 1, wherein the step of seeding the mesenchymal stem cells onto the inner layer and outer layer, respectively, of the tube-type porous biodegradable scaffold having a triple layered structure comprises the steps of:

a) suspending mesenchymal stem cells into an endothelial cell culture solution, and seeding the cell culture solution containing the mesenchymal stem cell onto the inner layer of the tube-type porous biodegradable scaffold having a triple layered structure;

b) fixing the mesenchymal stem cells to the inner layer of the tube-type porous biodegradable scaffold having a triple layered structure by rotating the tube-type porous biodegradable scaffold having a triple layered structure of step a) at the speed of 0.5 to 5 rpm for 1 to 6 hours;

c) suspending the mesenchymal stem cells into a smooth muscle culture solution, and seeding the culture solution containing the mesenchymal stem cells onto the outer layer of the tube-type porous biodegradable scaffold having a triple layered structure of step b); and d) fixing the mesenchymal stem cells to the outer layer of the tube-type porous biodegradable scaffold having a triple layered structure by rotating the tube-type porous biodegradable scaffold having a triple layered structure of step c) at the speed of 0.5 to 5 rpm for 15 to 30 hours.

3. The method of claim 1, wherein, in the step of applying shear stress, the mesenchymal stem cell-seeded tube-type porous biodegradable scaffold having a triple layered structure is immersed into the endothelial cell culture solution, and the shear stress of 2 dyne/cm$^2$ to 5 dyne/cm$^2$ per unit area of the mesenchymal stem cell-seeded tube-type porous biodegradable scaffold having a triple layered structure for 20 to 30 hours by flow of the endothelial cell culture solution.

4. An artificial blood vessel made by a method according to claim 1.

5. The artificial blood vessel of claim 4, whose diameter is 2 mm to 5 mm.

6. The artificial blood vessel of claim 4, which comprises vascular endothelial cells differentiated from mesenchymal stem cells at the inner layer, and smooth muscle cells differentiated from mesenchymal stem cells at the outer layer.

* * * * *